US009801862B2

(12) United States Patent
Garcia-Sánchez et al.

(10) Patent No.: US 9,801,862 B2
(45) Date of Patent: Oct. 31, 2017

(54) IMMUNOSUPPRESSIVE TREATMENTS, FORMULATIONS AND METHODS

(71) Applicants: Gustavo A. Garcia-Sánchez, Col. del Valle (MX); María Josefa Bernad Bernad, Colonia Lomas Estrella (MX)

(72) Inventors: Gustavo A. Garcia-Sánchez, Col. del Valle (MX); María Josefa Bernad Bernad, Colonia Lomas Estrella (MX)

(*) Notice: Subject to any disclaimer, the term of this patent is extended or adjusted under 35 U.S.C. 154(b) by 0 days.

(21) Appl. No.: 15/034,098

(22) PCT Filed: Nov. 5, 2014

(86) PCT No.: PCT/IB2014/002348
§ 371 (c)(1),
(2) Date: May 3, 2016

(87) PCT Pub. No.: WO2015/068020
PCT Pub. Date: May 14, 2015

(65) Prior Publication Data
US 2016/0271115 A1  Sep. 22, 2016

Related U.S. Application Data
(60) Provisional application No. 61/899,934, filed on Nov. 5, 2013.

(51) Int. Cl.
| | | |
|---|---|---|
| *A61K 9/127* | (2006.01) | |
| *A61K 31/436* | (2006.01) | |
| *A61K 45/06* | (2006.01) | |
| *A61K 9/00* | (2006.01) | |
| *A61K 9/10* | (2006.01) | |
| *A61K 47/24* | (2006.01) | |
| *A61K 47/28* | (2006.01) | |

(52) U.S. Cl.
CPC .......... *A61K 31/436* (2013.01); *A61K 9/0019* (2013.01); *A61K 9/0048* (2013.01); *A61K 9/0051* (2013.01); *A61K 9/10* (2013.01); *A61K 9/127* (2013.01); *A61K 9/1277* (2013.01); *A61K 45/06* (2013.01); *A61K 47/24* (2013.01); *A61K 47/28* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | |
|---|---|---|
| 7,083,802 B2 | 8/2006 | Peyman |
| 8,551,952 B2 | 10/2013 | Houck |
| 2004/0198829 A1 | 10/2004 | Sponsel |
| 2006/0263409 A1 | 11/2006 | Peyman |

FOREIGN PATENT DOCUMENTS

| | | | |
|---|---|---|---|
| CN | 102178649 | | 9/2011 |
| CN | 102178649 A | * | 9/2011 |
| WO | 1992010166 | | 6/1992 |
| WO | 2005084641 | | 9/2005 |

OTHER PUBLICATIONS

Google Machine Translation of Chinese patent CN 102178649 A. Obtained by Examiner from https://www.google.com/patents/CN102178649A?cl=en&dq=rapamycin+liposome&hl=en&sa=X&ved=0ahUKEwjV5bjU5IrQAhWohVQKHVOOAs8Q6AEIGzAA on Nov. 2, 2016. Original Patent published in Sep. 2011. 3 printed pages.*
MR Mozafari. "Nanoliposomes: Preparation and Analysis." Methods in Molecular Biology, vol. 605, Chapter 2, Copyright 2010, pp. 29-50. Obtained by examiner from http://link.springer.com/protocol/10.1007%2F978-1-60327-360-2_2#p. 1 on Nov. 3, 2016.*
C Chen, D Han, C Cai, X Tang. "An overview of liposome lyophilization and its future potential." Journal of Controlled Release, vol. 142, 2010, pp. 299-311.*
International Search Report and Written Opinion dated May 22, 2015 in Application No. PCT/IB2014/002348.
Ikeda et al., Tacrolimus-rapamycin combination therapy for experimental autoimmune uveoretinitis, Jpn J. Ophthalmol, Dec. 1997, vol. 41, No. 6, pp. 396-402.
International Preliminary Report on Patentability dated Oct. 21, 2015 in Application No. PCT/IB2014/002348.
Mortazavi et al., "Preparation of liposomal gene therapy vectors by a scalable method without using volatile solvents or detergents," Journal of Biotechnology 129, 2007, pp. 604-613, Elsevier.
Lee et al., "Application for Tacrolimus Ointment in Treating Refractory Inflammatory Ocular Surface Diseases," American Journal of Ophthalmology vol. 155 No. 5, 2013, pp. 804-813, Elsevier.
Nguyen et al., "Ocular tolerability and efficacy of intravitreal and subconjunctival injections of sirolimus in patients with non-infectious uveitis: primary 6-month results of the SAVE Study," Journal of Ophthalmic Inflammation and Infection 3:32, 2013, pp. 1-15, Springer.
Sen et al., "Subconjunctival Sirolimus for the Treatment of Chronis Active Anterior Uveitis: Results of a Pilot Trial," American Journal of Ophthalmology vol. 153 No. 6, Jun. 2012, pp. 1-8, National Institute of Health.
Ibrahim et al., "One-Year Outcomes of the SAVE Study: Sirolimus as a Therapeutic Approach for UVEitis," Translational Vision Science & Technology vol. 4 No. 2, 2015, pp. 1-13.
Alipour, et al., "Liposome-Entrapped Antibiotics: Recent Progress and Clinical Applications," Nanomedical Device and Systems Design, pp. 455-490, Aug. 27, 2013.
Mozafari, et al., "Construction of Stable Anionic Liposome-Plasmid Particle Using the Heating Method: A Preliminary Investigation," Cellular & Molecular Biology Letters, vol. 7, pp. 923-927, 2002.
Colas, et al., "Microscopial investigations of nisin-loaded nanoliposomes prepared by Mozafari method and their bacterial targeting," Micron, vol. 38, pp. 841-847, 2007.

\* cited by examiner

*Primary Examiner* — Isaac Shomer
(74) *Attorney, Agent, or Firm* — Snell & Wilmer L.L.P.

(57) ABSTRACT

The present disclosure provides inventive methods and formulations for immunosuppressive therapy for dry eye and other related immune mediated eye diseases. The formulations can comprise one or more immunomodulatory drugs such as parenterally administered liposome encapsulated rapamycin and topically administered tacrolimus. Immunomodulatory drugs herein can be formulated and administered to address the causes and/or reduce the symptoms of dry eye and/or other related immune mediated diseases of the eye.

9 Claims, No Drawings

IMMUNOSUPPRESSIVE TREATMENTS, FORMULATIONS AND METHODS

CROSS-REFERENCE TO RELATED APPLICATIONS

This application is U.S. national phase filing under 35 U.S.C. §371 of PCT/IB2014/002348 filed on Nov. 5, 2014 and entitled "IMMUNOSUPPRESIVE TREATMENTS, FORMULATIONS AND METHODS," which claims priority from U.S. Provisional Application No. 61/899,934 filed on Nov. 5, 2013 and entitled "COMPOSITIONS AND METHODS FOR DRUG DELIVERY." Both of the aforementioned applications are incorporated herein by reference in their entirety.

FIELD

The present disclosure relates to immunosuppressive methods, pharmacologic treatment formulations, and immunosuppressive treatments for immune mediated diseases of the tear film and cornea of the eye.

BACKGROUND

Ophthalmic tear film disorders or dry eye can be caused by traumatic orbital injury to the neural innervation or circulation to the lacrimal or tear gland, lacrimal gland neoplasia, congenital lacrimal gland disease, endocrine disease, and immune mediated eye and systemic diseases that affect the lacrimal gland. Lymphocytic invasion of the lacrimal gland results in quantitative and qualitative tear film disease. Immune mediated dry eye conditions include but are not limited to keratoconjunctivitis sicca (KCS) and Sjögren's syndrome (SS). Persistent corneal erosions and conjunctivitis can accompany KCS. Clinical signs of KCS include ocular discomfort, blurred vision, mucoid ocular discharge, conjunctival hyperemia, tear film instability, blepharospasm, recurrent corneal erosion and ulceration, corneal vascularization and pigmentation, and can ultimately lead to blindness if treatment is ineffective.

Treatments for dry eye and other related immune mediated diseases of the eye include anti-inflammatory drugs, antibiotics, antiproteases, artificial tears, and immunomodulatory drugs. Therapy may not be effective due to ocular irritation caused specifically by the fact the topical drug used is inherently irritating or the drug formulation is irritating. Poor ocular corneal contact time can result in poor drug bioavailability, and systemic absorption of the topical drug can also cause, low tear film and corneal drug levels. Failure of the drug to return tear production to normal levels may occur if the specific drug is not sufficiently able to prevent the immune mediated attack on the lacrimal gland. Poor drug stability, incorrect drug pH, variation in reproducibility of batch-to-batch dry eye drug production, difficulties in drug sterilization during drug production, low drug loading in sustained release techniques, and/or limitations for large-scale drug production are also problems in pharmacologic production of drugs for the treatment of dry eye and other related immune mediated diseases of the eye.

There is thus a continued need for improved immunosuppressive treatments, formulations and methods for the treatment of dry eye and/or other related immune mediated diseases of the eye.

SUMMARY

The present disclosure provides inventive methods and formulations for immunosuppressive therapy for dry eye and other related immune mediated eye diseases. In example embodiments, the formulations comprise one or more immunomodulatory drugs such as liposome encapsulated rapamycin and tacrolimus, which can be administered, parenterally and topically respectively. Such drugs can be formulated and administered to address the causes and/or reduce the symptoms of dry eye and/or other related immune mediated diseases of the eye.

DETAILED DESCRIPTION

The present disclosure includes immunosuppressive treatments, formulations and methods for the treatment of dry eye and/or other related immune mediated diseases of the eye. Persons skilled in the art will readily appreciate that various aspects of the disclosure may be realized by any number of treatments, formulations and methods configured to perform the intended functions. Stated differently, other treatments, formulations and methods may be incorporated herein to perform the intended functions. Although the present disclosure may be in connection with various medical principles and beliefs, the present disclosure should not be bound by theory.

The term "approximately," as used in this specification and appended claims, refers to plus or minus 5% of the value given. The term "about," as used in this specification and appended claims, refers to plus or minus 10% of the value given.

While the present disclosure will be described primarily with reference to KCS or dry eye, persons skilled in the art will readily appreciate that the teachings herein may be applied more broadly in iritis, cyclitis, anterior uveitis, phacoanaphylactic endophthalmitis, uveodermatologic syndrome and other immune mediated diseases of the eye. Teachings in this disclosure can also have application to cancer therapy, and the therapy of systemic immunologic diseases including but not limited to Addison's disease, celiac disease, dermatomyositis, Graves' disease, Hashimoto's thyroiditis, multiple sclerosis, myasthenia gravis, pernicious anemia, reactive arthritis, rheumatoid arthritis, systemic lupus erythematosus, and type I diabetes.

Persons skilled in the art will further appreciate that the teachings herein may be applied to human as well as animal subjects (e.g., dogs, rabbits, cats, horses, primates or other domestic or wild subjects), young subjects and adult subjects, and male and female subjects.

An example of a typical immunosuppressive treatment comprises a primary formulation, which may be administered by itself or together with a secondary formulation. When primary and secondary formulations are administered together, they can be administered in the same pharmaceutical form (e.g., compounded together), or can be administered in different pharmaceutical forms alone or substantially contemporaneously one with another.

By way of example, a primary formulation can be administered before or after a secondary formulation, administration of primary and secondary formulations can be staggered, and the frequency of administration of primary and secondary formulations can be the same or different.

A suitable route of administration or drug form for either or both of the primary and secondary formulations can be topical (e.g., eye drop solution, eye drop suspension, eye drop ointment, eye drop cream), oral (e.g., tablet, capsule) or parenteral (e.g., subconjunctival injection). Importantly, the primary and secondary formulations can be administered through the same or different route of administration or drug form.

Either or both of the primary and secondary formulations can comprise one or more immunomodulatory drugs. Examples include rapamycin (molecular weight 914.17, $C_{51}H_{79}NO_{13}$, also known in the art as sirolimus), calcineurin inhibitors, including but not limited to tacrolimus (molecular weight 804.02, $C_{44}H_{69}NO_{12}$, also known in the art as FK506) and cyclosporine A (molecular weight 1202.61, $C_{62}H_{111}N_{11}O_{12}$), lacrimogenic and immunosuppressant medications, antibody production suppressors, and other T and B lymphocyte activation or proliferation inhibitors.

One or more immunomodulatory drugs can be present in a stable formulation in a suitable amount depending on the targeted tissue, the physicochemical properties of the active compound to be used, and the desired kinetic of ocular release. Without intending to limit the foregoing, in example embodiments, an immunomodulatory drug can be present in an amount of about 0.01% (g/ml) to about 0.2% (g/ml), or more preferably about 0.04% (g/ml) to about 0.1% (g/ml).

In example embodiments, the primary and secondary formulations comprise complementary immunomodulatory drugs. Indeed, the inventors have found that rapamycin and tacrolimus have a synergistic effect when used together in a common stable, long acting, immunosuppressive treatment achieving effective ophthalmic therapy, reaching adequate amount of ingredients, maintaining therapeutic drug dose levels at the site of action for long times within the eye, and minimizing undesirable systemic side effects.

In various embodiments, the synergistic effect results in the required dose for each being reduced and thus reducing undesirable systemic side effects. Without intending to be bound by theory, the synergistic effect can refer to shared metabolism (e.g., by CYP 3A), shared cytosolic binding protein (e.g., FKBP), common or complimentary regulation of T lymphocyte and B lymphocyte activation or proliferation, common or complimentary immune and/or inflammatory response pathway mediation, or other nonlinear effect or mutualism of a plurality of immunomodulatory drugs.

In this regard, an example immunosuppressive treatment consists of, or consists essentially of, rapamycin and tacrolimus. Put another way, an example immunosuppressive treatment does not comprise cyclosporine A or any other T lymphocyte and B lymphocyte activation or proliferation inhibitor. In yet other embodiments, an immunosuppressive treatment comprises a first immunomodulatory drug that is a non-calcineurin inhibitor, and a second immunomodulatory drug that is a calcineurin inhibitor.

In addition to an immunomodulatory drug, either or both of the primary and secondary formulations can comprise one or more dispersion vehicle solvents and dispersant agents, for example, saline solutions, e.g., phosphate buffer saline (PBS), aqueous dextrose and glycerol solutions, ethanol, and the like. One or more dispersion vehicle solvents and dispersant agents can be present in a formulation in an amount of up to about 99.97%.

Either or both of the primary and secondary formulations can also comprise one or more excipients, for example, olive oil, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. One or more excipients can be present in a formulation in an amount of up to about 99.97%.

Delivery of either or both of the primary and secondary formulations can be facilitated with a carrier, for example, liposomes or other nanocarriers. As used herein, a "liposome" is any microscopic vesicle comprised of a lipid bilayer (or many lipid bilayers) surrounding an aqueous core that can enhance the solubilization and absorption of an encapsulated drug while protecting the drug from premature degradation and increasing residence time of the drug inside the body.

In example embodiments, liposomes can comprise one or more of lecithin (e.g., soybean or sunflower derived) or other phospholipids (e.g., dimyristoylphosphatidylcholine or dipalmitoylphosphatidylcholine), cholesterol and a cryoprotector (e.g., sucrose or trehalose).

Liposomes herein (e.g., obtained by adapting the heating method as discussed infra), have diameters ranging from about 135 nm to about 215 nm, or more preferably from about 180 nm to about 200 nm, with an entrapment efficiency of from about 90% to about 99.5%, or more preferably from about 93% to about 98%. In example embodiments, liposomes herein can have a phospholipid concentration of from about 1 mM to about 10 mM, or more preferably about 5 mM.

In yet other embodiments, delivery of a formulation can be targeted to a particular cell or region of interest. In addition, or in the alternative, a formulation can be configured to remain in contact or in close proximity to a particular cell or region of interest for an extended period of time.

Methods of making immunosuppressive treatments and formulations are also provided herein. In an example embodiment, liposomes are loaded with an immunomodulatory drug, for example rapamycin. Liposomes for use with an immunomodulatory drug herein can be prepared using the ethanol injection method or the heating method, both as known by persons skilled in the art. In other embodiments, liposomes can be prepared using an inventive adaptation of the heating method.

In an example embodiment of such adaptation, cholesterol and lecithin are hydrated with PBS for 1 hr under $N_2$, the former at 80° C. and the latter at room temperature. The lipid dispersions are then mixed together with the desired rapamycin amount in the presence of glycerol (3% v/v) and the volume made up to 10 mL. The mixture is heated to 70° C. while stirring at 750 rpm for 30 min. The resultant dispersion is left at room temperature under $N_2$ for 30 min. The dispersion is extruded with a stainless steel pressure filter holder (Millipore Co., U.S.A.) through polyvinylidene fluoride (PVDF) hydrophilic membrane of 0.45 µm pore size (Durapore HVLP, Millipore Co., U.S.A.) with a $N_2$ pressure inlet of 2 bars. In example embodiments, the extrusion step is conducted at a temperature above the phase transition temperature of the phospholipids. Example methods of making also comprise a freeze drying step, by freezing the sample in liquid nitrogen, a primary drying at −45° C. at maximum power vacuum ($2 \times 10^{-3}$ mBar) followed by a secondary drying at 25° C. at maximum power vacuum. Finally, the dispersion is sterilized, collected in amber glass sterile vials and kept in refrigeration until use. In example embodiments, the use of an adaptation of the heating method developed by the inventors does not comprise the use of any organic solvents or surfactants in the manufacturing process, minimizes toxicity, shortens manufacturing time, reduces cost, and/or allows industrial production scaling.

Methods of use of immunosuppressive treatments and formulations are also provided herein. In example embodiments, a topical formulation can be administered from about every 4 hours to about every 12 hours, an oral formulation can be administered from about every 12 hours to about every 2 days, and a parenteral formulation can be administered from about every 2 days to about every 30 days. Notwithstanding the foregoing, persons skilled in the art will appreciate that longer or shorter dosing intervals may be appropriate depending on the concentrations and indications.

As a non-limiting example of an immunosuppressive treatment and method of use of the same, an example primary formulation comprises a suspension of approximately 0.4 mg/ml or 1.0 mg/ml rapamycin encapsulated in soybean lecithin, cholesterol and sucrose liposomes, and glycerol, the balance comprised of PBS with a pH of approximately 7.45, as set forth in Table I.

TABLE I

Example Primary Formulation A

| Ingredient | Weight/Volume Percentage (g/ml) |
| --- | --- |
| Rapamycin | 0.04-0.1% |
| Cholesterol | 0.077-1.01% |
| Lecithin | 0.23-3.05% |
| Glycerol | 2.4% |
| Sucrose | 0.92-12.2% |
| PBS | Quantity sufficient for 100% |

The formulation of Table I is then administered in an amount of approximately 0.15 ml via subconjunctival injection every 15 days for 2 months or until instructed by a physician.

Yet another example of a primary formulation is set forth in Table II.

TABLE II

Example Primary Formulation B

| Ingredient | Weight/Volume Percentage (g/ml) |
| --- | --- |
| Rapamycin | 0.04% |
| Cholesterol | 0.404% |
| Lecithin | 1.22% |
| PBS | Quantity sufficient for 100% |

An example secondary formulation of the same immunosuppressive treatment comprises a suspension of approximately 0.03% tacrolimus in olive oil. The formulation is administered in an amount of approximately one eye drop every 8 hours for 2 months or until instructed by a physician.

Example immunosuppressive treatments, formulations and methods for the treatment of dry eye were tested in a clinical trial, and the results were unexpected and surprising.

The objective of the trial was to evaluate the combination of topically administered tacrolimus and liposome encapsulated rapamycin in dogs with severe KCS nonresponsive to conventional medical therapy.

Seventeen dogs (29 eyes) were studied with a Schirmer tear test I value of less than 5 mm wetting/minute.

The eyes received a subconjunctival injection of liposomes with rapamycin at a dose of 0.4 mg/ml every 15 days for two months. Topically administered medication of 0.03% tacrolimus was also utilized, one drop every 8 hours. Complete ophthalmologic evaluation using a modified McDonald-Shadduck protocol that included Schirmer tear tests (STT) I and II and tear film break up time (TFBUT) were made every 15 days.

The McDonald-Shadduck protocol is described in the following references, each of which is incorporated by reference herein in its entirety for all purposes. Hackett, R. B., & McDonald, T. O. (1991). Eye irritation. HEMISPHERE PUBLISHING CORPORATION, NEW YORK, N.Y. (USA)., 749-815. Gritz, D. C., McDonnell, P. J., Lee, T. Y., Tang-Liu, D., Hubbard, B. B., & Gwon, A. (1992). Topical Ofloxacin in the Treatment of *Pseudomonas* Keratitis in a Rabbit Mode. Cornea, 11(2), 143-147. York K K, Miller S, Gaster R N, Burstein N L. Polyvinylpyrrolidone iodine: corneal toxicology and epithelial healing in a rabbit model. J Ocul Pharmacol. 1988 Winter; 4(4):351-8.

STT is described in the following references, each of which is incorporated by reference herein in its entirety for all purposes. Schirmer O. Studien zur physiologie und pathologie der traneabsonderung und tranenabfuhr. Graefes Archiv für Klinische und Experimentische Ophthalmologie 1903; 56: 197-291. Williams, D. L. (2005). Analysis of tear uptake by the Schirmer tear test strip in the canine eye. Veterinary ophthalmology, 8(5), 325-330. Gelatt K N, Peiffer N L, Erickson J L, Gum G G. Evaluation of tear formation in the dog using a modification of the Schirmer tear test. J American Veterinary Medical Association 1975; 166: 368-370.

TFBUT is described in the following references, each of which is incorporated by reference herein in its entirety for all purposes. Moore C P, for M M Wilsman N J, Nordheim E V, et al: Density and distribution of canine conjunctival goblet cells, Invest Ophthalmol Vis Sci 1987; 28: 1925-1932. Kallarackal, G. U., Ansari, E. A., Amos, N., Martin, J. C., Lane, C., & Camilleri, J. P. (2002). A comparative study to assess the clinical use of Fluorescein Meniscus Time (FMT) with Tear Break up Time (TBUT) and Schirmer's tests (ST) in the diagnosis of dry eyes. Eye, 16(5), 594-600. Cho, P., Leung, L., Lam, A., & Choi, A. (1998). Tear break-up time: clinical procedures and their effects. Ophthalmic and Physiological Optics, 18(4), 319-324.

The modified McDonald-Shadduck score system is a slit lamp scale for scoring ocular irritation that uses also indirect ophthalmoscopy and neuro-ophthalmic reflexes for ocular media clarity. It graduates in a 0 to 4 score (0 is the normality and 4 maximum alteration): clarity of ocular media, eyelids, cornea, % area of corneal opacity, corneal vascularization, conjunctival congestion, conjunctival chemosis/swelling, conjunctival discharge (color and consistency), aqueous flare, aqueous cell, cell color, iris and lens.

During the trial, as shown in Tables III-V below, it was observed that STT I and II, and the TFBUT improved significantly during the 2 month treatment period (P<0.001). Clinical signs improved significantly with reduction in corneal opacity (p<0.001), conjunctival congestion (P<0.001), conjunctival chemosis (P<0.001) and conjunctival discharge (P<0.001). The modified McDonald-Shadduck results also displayed statistically significant improvement (P<0.001).

TABLE III

Shirmer tear test I and II, Median mm/min (min value; max value)

| | Day after initiation of treatment | | | | | |
| --- | --- | --- | --- | --- | --- | --- |
| | 0 | 15 | 30 | 45 | 60 | P value |
| STT I | 1.5 (0.0; 4.0)a | 4.0 (0.0; 15.0)ab | 4.0 (0.0; 21.0)bc | 4.5 (0.0; 20.0)c | 6.0 (0.0; 21.0)d | P < 0.001 |
| STT II | 0.0 (0.0; 4.0)a | 0.0 (0.0; 10.0)ab | 0.0 (0.0; 11.0)ab | 1.5 (0.0; 13.0)b | 2.0 (0.0; 13.0)b | P < 0.001 |

STT—Schirmer tear test
Equal letters - no significant difference
Different letters - significant difference

TABLE IV

Tear film break up time, Median sec (min value; max value)

| | Day after initiation of treatment | | | | | |
|---|---|---|---|---|---|---|
| | 0 | 15 | 30 | 45 | 60 | P value |
| TFBUT | 6.0 (4.0; 13.0)a | 10.0 (5.0; 21.0)b | 10.0 (5.0; 25.0)bc | 10.0 (5.0; 25.0)bc | 11.0 (6.0; 25.0)c | p < 0.001 |

TFBUT—tear film break up time
Equal letters - no significant difference
Different letters - significant difference

TABLE V

Modified McDonald-Shadduck test results, Median (min value; max value)

| | Day after initiation of treatment | | | | | |
|---|---|---|---|---|---|---|
| | 0 | 15 | 30 | 45 | 60 | P value |
| Eyelids | 1.0 (0.0; 2.0)b | 0.0 (0.0; 2.0)ab | 0.0 (0.0; 2.0)ab | 0.0 (0.0; 2.0)ab | 0.0 (0.0; 2.0)a | p < 0.001 |
| % CO | 2.0 (1.0; 4.0)b | 1.5 (1.0; 4.0)ab | 1.0 (0.0; 3.0)ab | 1.0 (0.0; 3.0)ab | 1.0 (0.0; 3.0)a | p < 0.001 |
| CC | 2.0 (0.0; 2.0)c | 1.0 (0.0; 2.0)b | 1.0 (0.0; 2.0)ab | 0.5 (0.0; 2.0)ab | 0.0 (0.0; 1.0)a | p < 0.001 |
| CCh | 1.0 (0.0; 2.0)b | 0.0 (0.0; 2.0)a | 0.0 (0.0; 2.0)a | 0.0 (0.0; 2.0)a | 0.0 (0.0; 2.0)a | p < 0.001 |
| CD | 2.0 (1.0; 3.0)c | 1.0 (0.0; 2.0)b | 1.0 (0.0; 2.0)b | 1.0 (0.0; 2.0)ab | 1.0 (0.0; 2.0)a | p < 0.001 |
| CDCC | 2.0 (1.0; 3.0)c | 1.0 (0.0; 2.0)b | 1.0 (0.0; 2.0)b | 1.0 (0.0; 2.0)ab | 1.0 (0.0; 2.0)a | p < 0.001 |

% CO, % area of corneal opacity
CC, conjunctival congestion
CCh, conjunctival chemosis
CD, conjunctival discharge
CDCC, conjunctival discharge color and consistence
Equal letters - no significant difference
Different letters - significant difference In the trial, the treatment used did not cause ocular irritation or other side effects in any animal studied. The association of topical tacrolimus with liposomes containing rapamycin was effective in alleviating the clinical signs of KCS in dogs, as well as increased tear production and tear film quality of the studied animals.

Treatments, formulations and methods are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The foregoing disclosure is merely illustrative of the present disclosure and is not intended to be construed as limiting the invention. Although one or more embodiments of the invention have been described, persons skilled in the art will readily appreciate that numerous modifications could be made without departing from the spirit and scope of the present disclosure. By way of example, a formulation in accordance with the present disclosure can comprise, consist essentially of, or consisting of, any combination of the ingredients described above. As such, it should be understood that all such modifications are intended to be included within the scope of the disclosure.

We claim:

1. A method of making an immunosuppressive formulation for administration to an eye by a modified heating method, comprising the steps of:
    hydrating cholesterol to create a cholesterol dispersion;
    hydrating lecithin and sucrose to create a lecithin dispersion;
    creating a mixture comprising the cholesterol dispersion, the lecithin dispersion, and rapamycin; and
    simultaneously heating and stirring the mixture to create a dispersion of liposomes loaded with rapamycin.

2. The method of claim 1, wherein the lecithin is comprised of soybean derived lecithin.

3. The method of claim 1, wherein the step of hydrating cholesterol to create the cholesterol dispersion comprises hydrating cholesterol with PBS for 1 hr under N2 at 80° C.

4. The method of claim 3, wherein the step of hydrating lecithin to create the lecithin dispersion comprises hydrating lecithin with PBS for 1 hr under N2 at room temperature.

5. The method of claim 4, wherein the step of simultaneously heating and stirring the mixture to create the dispersion of liposomes comprises heating to 70° C. while stirring at 750 rpm for 30 min.

6. The method of claim 5, further comprising a step of leaving the dispersion of liposomes at room temperature under N2 for 30 min.

7. The method of claim 1, wherein simultaneously heating and stirring the mixture to create the dispersion of liposomes loaded with rapamycin comprises forming liposomes that have an average diameter between about 135 nm to about 215 nm.

8. A method of making an immunosuppressive formulation for administration to an eye by a modified heating method, comprising the steps of:
   hydrating cholesterol to create a cholesterol dispersion;
   hydrating lecithin to create a lecithin dispersion;
   creating a mixture comprising the cholesterol dispersion, the lecithin dispersion, and rapamycin; and
   simultaneously heating and stirring the mixture to create a dispersion of liposomes loaded with rapamycin;
   wherein the mixture consists of:
   from approximately 0.04 to approximately 0.1% (g/ml) rapamycin;
   from approximately 0.077 to approximately 1.01% (g/ml) cholesterol;
   from approximately 0.23 to approximately 3.05% (g/ml) soybean lecithin;
   from approximately 0.92 to approximately 12.2% (g/ml) sucrose;
   approximately 2.4% (g/ml) glycerol; and
   phosphate buffered saline.

9. The method of claim 8, further comprising a step of freeze drying, wherein the sucrose acts as one of a lyoprotectant and cryoprotectant.

\* \* \* \* \*